(12) United States Patent
Padilla De Jesus et al.

(10) Patent No.: US 8,409,526 B2
(45) Date of Patent: Apr. 2, 2013

(54) CELLULOSE SUBSTRATES, COMPOSITIONS AND METHODS FOR STORAGE AND ANALYSIS OF BIOLOGICAL MATERIALS

(75) Inventors: Omayra Liz Padilla De Jesus, Clifton Park, NY (US); David Roger Moore, Rexford, NY (US); William Christopher Alberts, Saratoga Springs, NY (US)

(73) Assignee: General Electric Company, Niskayuna, NY (US)

( * ) Notice: Subject to any disclaimer, the term of this patent is extended or adjusted under 35 U.S.C. 154(b) by 85 days.

(21) Appl. No.: 12/964,363

(22) Filed: Dec. 9, 2010

(65) Prior Publication Data

US 2012/0149006 A1      Jun. 14, 2012

(51) Int. Cl.
*G01N 33/52* (2006.01)
(52) U.S. Cl. ............... 422/408; 435/805; 435/4; 435/5; 435/9; 422/420; 422/425; 422/68.1; 436/174; 536/30; 536/56
(58) Field of Classification Search .................. 422/547, 422/420, 425, 68.1, 408; 435/805, 4, 5, 29; 106/163.01; 536/30, 56; 436/174
See application file for complete search history.

(56) References Cited

U.S. PATENT DOCUMENTS

| | | | |
|---|---|---|---|
| 5,414,079 A | 5/1995 | Banker et al. |
| 6,627,226 B2 | 9/2003 | Burgoyne et al. |
| 6,645,717 B1 | 11/2003 | Smith et al. |
| 6,716,976 B1 | 4/2004 | Jetten et al. |
| 2004/0028664 A1 | 2/2004 | Blakesley et al. |
| 2006/0058513 A1 | 3/2006 | Papisov et al. |
| 2008/0196517 A1 | 8/2008 | Harvey et al. |

FOREIGN PATENT DOCUMENTS

| | | |
|---|---|---|
| EP | 0815879 A2 | 1/1998 |
| RU | 2364604 C1 | 8/2009 |
| WO | WO9641813 A2 | 12/1996 |
| WO | 02088189 A2 | 11/2002 |
| WO | 2008013735 A2 | 1/2008 |

OTHER PUBLICATIONS

Li et al., "Dried Blood Spot Sampling in Combination With LC-MS/MS for Quantitative Analysis of Small Molecules", Biomedical Chromatography, Special Issue: Review, vol. 24, pp. 49-65, 2010.

(Continued)

*Primary Examiner* — Jill Warden
*Assistant Examiner* — Monique Cole
(74) *Attorney, Agent, or Firm* — Eileen B. Gallagher

(57) ABSTRACT

The invention provides a method and article for storing genetic material or analytes from a biological sample by contacting said biological sample with a cellulose substrate comprising structural units of Formula I

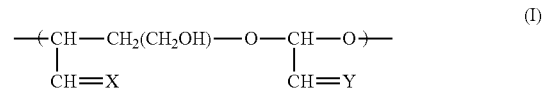

wherein X and Y are independently N—O-L-A or O, with the proviso that when Y is O, then X is N—O-L-A, and when X is O, then Y is N—O-L-A; L is a direct bond, an aliphatic radical, an aromatic radical, a cycloaliphatic radical, or a combination thereof; and A=COOH, SO3H, or a combination thereof. The invention also relates to a cellulose substrate comprising the structural units of Formula I, and a method of manufacturing the same.

9 Claims, 2 Drawing Sheets

Figure 1:
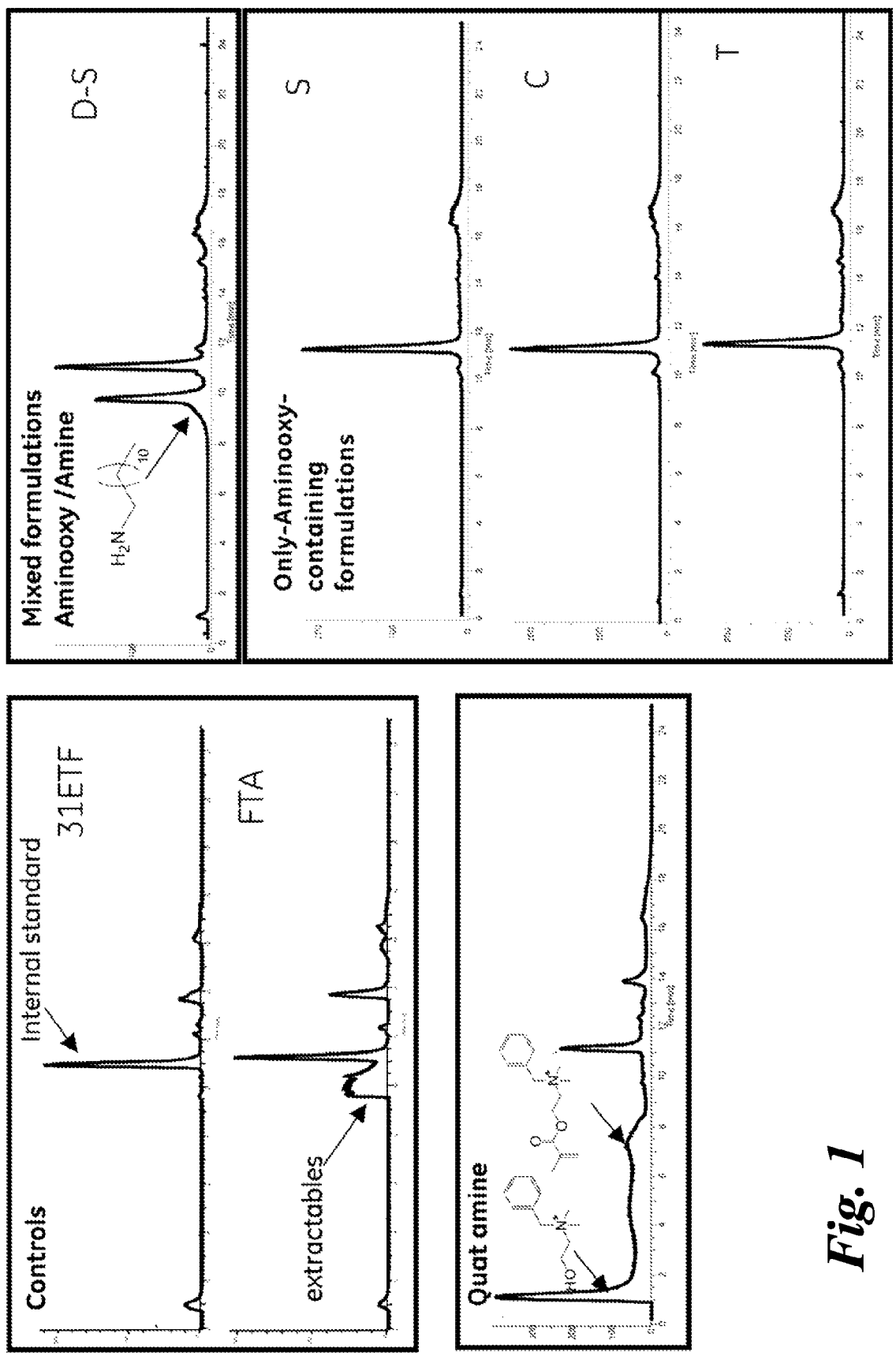

OTHER PUBLICATIONS da Silva Fiho et al., "Cation Removal Using Cellulose Chemically Modified by a Schiff Base Procedure Applying Green Principles", Journal of Colloid and Interface Science, vol. 340, pp. 8-15, 2009.

Barfield et al., "Application of Dried Blood Spots Combined With HPLC-MS/MS for the Quantification of Acetaminophen in Toxicokinetic Studies", Journal of Chromatography B, vol. 870, pp. 32-37, 2008.

Fras et al., "Analysis of the Oxidation of Cellulose Fibres by Titration and XPS", Colloids and Surfaces A: Physicochem. Eng. Aspects, vol. 260, pp. 101-108, 2005.

Spooner et al., "Dried Blood Spots as a Sample Collection Technique for the Determination of Pharmacokinetics in Clinical Studies: Considerations for the Validation of a Quantitative Bioanalytical Method", Anal. Chem., vol. 81, pp. 1557-1563, 2009.

Kim et al., Thermal Decomposition of Dialdehyde Cellulose and its Nitrogen-Containing Derivatives, Thermochimica Acta, vol. 369, pp. 79-85, 2001.

Nedospasov et al., "Synthesis and Some Properties of Aminooxyalkycelluloses", Institute of Molecular Biology, Academy of Sciences of the USSR, Moscow, pp. 1105-1110, May 1976.

Segall et al., "The Action of Hydroxylamine, Its 0-Methyl Ether, and Their Hydrochlorides on Cellulose Trinitrate in Pyridine" Canadian Journal of Chemistry, vol. 30, pp. 860-871, 1952.

Search Report and Written Opinion from corresponding PCT Application No. PCT/SE2011/051484 dated Mar. 9, 2012.

Sirvio, "Periodate oxidation of cellulose at elevated temperatures using metal salts as cellulose activators" In: Carbohydrate polymers, pp. 1293-1297, Sep. 24, 2010.

CELLULOSE SUBSTRATES, COMPOSITIONS AND METHODS FOR STORAGE AND ANALYSIS OF BIOLOGICAL MATERIALS

BACKGROUND

FTA® paper (GE Healthcare, Whatman Inc., Piscataway, N.J.) has proven to be a reliable means of collecting, transporting, storing, and archiving genetic material, such as DNA, from a variety of biological samples. Simple procedures have been developed and widely used for purification and amplification of samples stored on FTA. Newer procedures have also been developed using FTA molecular procedures, such as drug metabolism and pharmacokinetic (DMPK) analysis including toxicokinetics (TK) studies. In many cases analysis may be performed directly on the paper containing the immobilized DNA sample. In other cases, the DNA may first be eluded from the paper, whereby the DNA is released into solution (FTA Elute®). Elution may occur through various washing cycles using solutions capable of solubilizing the DNA and may also including applying heat, vacuum, or centrifugation to the process.

Although current FTA paper provides attractive properties, such as stabilization of components of interest and antibacterial features that enable lower safety guidelines, one disadvantages of the current FTA paper, as applied to DMPK and TK type studies, is leachable components on the paper, which may interfere with the downstream analysis of drugs and metabolites, or other analytes.

In order to expand the use of FTA paper technology, a method of preserving the biological sample on paper is needed, without the problem of interfering leachables, and while maintaining other desirable features such as antibacterial properties and hydrophilic/wicking properties of the paper are maintained.

BRIEF DESCRIPTION

In one embodiment, the invention provides a method of storing genetic material or analytes from a biological sample by contacting said biological sample with a cellulose substrate said cellulose substrate comprising structural units of Formula I

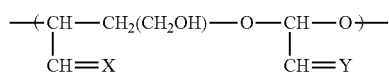

wherein X and Y are independently N—O-L-A or O, with the proviso that when Y is O, then X is N—O-L-A, and when X is O, then Y is N—O-L-A; L is a direct bond, an aliphatic radical, an aromatic radical, a cycloaliphatic radical, or a combination thereof; and A=COOH, $SO_3H$, or a combination thereof.

In one embodiment, the invention provides an article for storing genetic material or analytes from a biological sample comprising a cellulose substrate comprising the structural units of Formula I.

In another embodiment, the invention provides a cellulose substrate comprising structural units of Formula I and a method of manufacturing the same.

DRAWINGS

These and other features, aspects, and advantages of the present invention will become better understood when the following detailed description is read with reference to the accompanying drawings in which like characters represent like parts throughout the drawings.

FIG. 1 is LC-MS trace of extractables from papers treated using different surface chemistries and formulations, including both positive (current FTA paper) and negative controls (unmodified paper).

Figure 2:
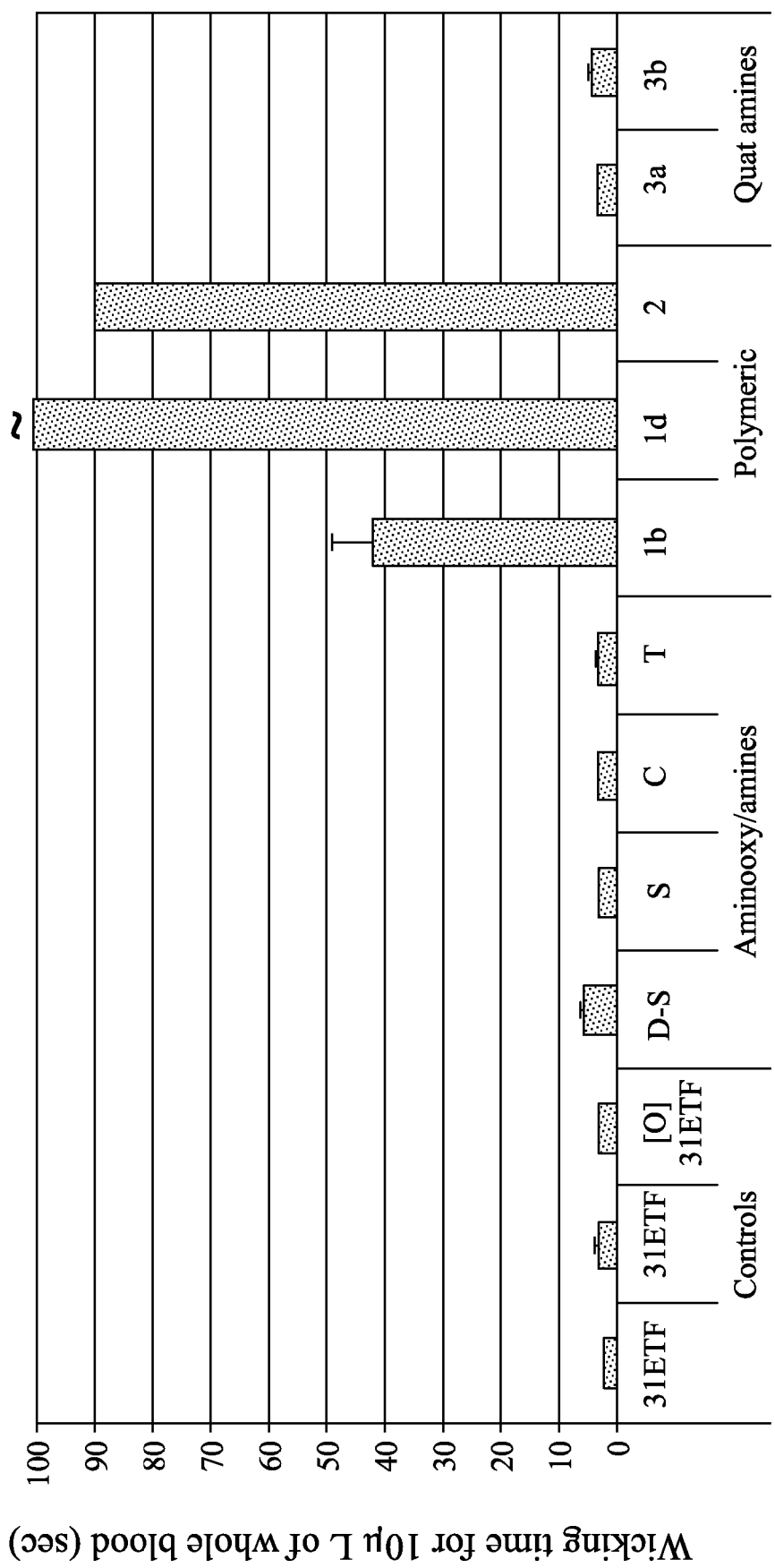

FIG. 2. is a graphical representation of wicking performance of a variety of papers treated with different chemistries and families of molecules; for the aminooxy/amine family, the corresponding oxidized paper is included as a control, in addition to the standard positive and negative control papers.

DETAILED DESCRIPTION

Definitions

To more clearly and concisely describe and point out the subject matter of the claimed invention, the following definitions are provided for specific terms that are used in the following description and the claims appended hereto.

Aliphatic radical is an organic radical having at least one carbon atom, a valence of at least one and may be a linear or branched array of atoms. Aliphatic radicals may include heteroatoms such as nitrogen, sulfur, silicon, selenium and oxygen or may be composed exclusively of carbon and hydrogen. Aliphatic radical may include a wide range of functional groups such as alkyl groups, alkenyl groups, alkynyl groups, halo alkyl groups, conjugated dienyl groups, alcohol groups, ether groups, aldehyde groups, ketone groups, carboxylic acid groups, acyl groups (for example, carboxylic acid derivatives such as esters and amides), amine groups, nitro groups and the like. For example, the 4-methylpent-1-yl radical is a $C_6$ aliphatic radical comprising a methyl group, the methyl group being a functional group, which is an alkyl group. Similarly, the 4-nitrobut-1-yl group is a $C_4$ aliphatic radical comprising a nitro group, the nitro group being a functional group. An aliphatic radical may be a haloalkyl group that includes one or more halogen atoms, which may be the same or different. Halogen atoms include, for example; fluorine, chlorine, bromine, and iodine. Aliphatic radicals having one or more halogen atoms include the alkyl halides: trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g., —$CH_2CHBrCH_2$—), and the like. Further examples of aliphatic radicals include allyl, aminocarbonyl (—$CONH_2$), carbonyl, dicyanoisopropylidene —$CH_2C(CN)_2CH_2$—), methyl (—$CH_3$), methylene (—$CH_2$—), ethyl, ethylene, formyl (—CHO), hexyl, hexamethylene, hydroxymethyl (—$CH_2OH$), mercaptomethyl (—$CH_2SH$), methylthio (—$SCH_3$), methylthiomethyl (—$CH_2SCH_3$), methoxy, methoxycarbonyl ($CH_3OCO$—), nitromethyl (—$CH_2NO_2$), thiocarbonyl, trimethylsilyl (($CH_3)_3Si$—), t-butyldimethylsilyl, trimethoxysilylpropyl (($CH_3O)_3SiCH_2CH_2CH_2$—), vinyl, vinylidene, and the like. By way of further example, a "$C_1$-$C_{30}$ aliphatic radical" contains at least one but no more than 30 carbon atoms. A methyl group ($CH_3$—) is an example of a $C_1$ aliphatic radical. A decyl group ($CH_3(CH_2)_9$—) is an example of a $C_{10}$ aliphatic radical.

A cycloaliphatic radical is a radical having a valence of at least one, and having an array of atoms, which is cyclic but which is not aromatic. A cycloaliphatic radical may include one or more non-cyclic components. For example, a cyclohexylmethyl group ($C_6H_{11}CH_2$—) is a cycloaliphatic radical, which includes a cyclohexyl ring (the array of atoms, which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. A cycloaliphatic radical may include one or more functional groups, such as alkyl groups, alkenyl groups, alkynyl groups, halo alkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups and the like. For example, the 4-methylcyclopent-1-yl radical is a $C_6$ cycloaliphatic radical comprising a methyl group, the methyl group being a functional group, which is an alkyl group. Similarly, the 2-nitrocyclobut-1-yl radical is a $C_4$ cycloaliphatic radical comprising a nitro group, the nitro group being a functional group. A cycloaliphatic radical may include one or more halogen atoms, which may be the same or different. Halogen atoms include, for example, fluorine, chlorine, bromine, and iodine. Cycloaliphatic radicals having one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene 2,2-bis(cyclohex-4-yl) ($-C_6H_{10}C(CF_3)_2C_6H_{10}-$), 2-chloromethylcyclohex-1-yl; 3-difluoromethylenecyclohex-1-yl; 4-trichloromethylcyclohex-1-yloxy, 4-bromodichloromethylcyclohex-1-ylthio, 2-bromoethylcyclopent-1-yl, 2-bromopropylcyclohex-1-yloxy (e.g. $CH_3CHBrCH_2C_6H_{10}-$), and the like. Further examples of cyclo aliphatic radicals include 4-allyloxycyclohex-1-yl, 4-aminocyclohex-1-yl ($H_2C_6H_{10}-$), 4-aminocarbonylcyclopent-1-yl ($NH_2COC_5H_8-$), 4-acetyloxycyclohex-1-yl, 2,2-dicyanoisopropylidenebis(cyclohex-4-yloxy) ($-OC_6H_{10}C(CN)_2C_6H_{10}O-$), 3-methylcyclohex-1-yl, methylenebis(cyclohex-4-yloxy) ($-OC_6H_{10}CH_2C_6H_{10}O-$), 1-ethylcyclobut-1-yl, cyclopropylethenyl, 3-formyl-2-terahydrofuranyl, 2-hexyl-5-tetrahydrofuranyl; hexamethylene-1,6-bis(cyclohex-4-yloxy) ($-OC_6H_{10}(CH_2)_6C_6H_{10}O-$); 4-hydroxymethylcyclohex-1-yl (4-$HOCH_2C_6H_{10}-$), 4-mercaptomethylcyclohex-1-yl (4-$HSCH_2C_6H_{10}-$), 4-methylthiocyclohex-1-yl (4-$CH_3SC_6H_{10}-$), 4-methoxycyclohex-1-yl, 2-methoxycarbonylcyclohex-1-yloxy (2-$CH_3OCOC_6H_{10}O-$), 4-nitromethylcyclohex-1-yl ($NO_2CH_2C_6H_{10}-$), 3-trimethylsilylcyclohex-1-yl, 2-t-butyldimethylsilylcyclopent-1-yl, 4-trimethoxysilylethylcyclohex-1-yl (e.g. $(CH_3O)_3SiCH_2CH_2C_6H_{10}-$), 4-vinylcyclohexen-1-yl, vinylidenebis (cyclohexyl), and the like. The term "a $C_3$-$C_{30}$ cycloaliphatic radical" includes cycloaliphatic radicals containing at least three but no more than 10 carbon atoms. The cycloaliphatic radical 2-tetrahydrofuranyl ($C_4H_7O-$) represents a $C_4$ cycloaliphatic radical. The cyclohexylmethyl radical ($C_6H_{11}CH_2-$) represents a $C_7$ cycloaliphatic radical.

An aromatic radical is an array of atoms having a valence of at least one and having at least one aromatic group. This may include heteroatoms such as nitrogen, sulfur, selenium, silicon and oxygen, or may be composed exclusively of carbon and hydrogen. Suitable aromatic radicals may include phenyl, pyridyl, furanyl, thienyl, naphthyl, phenylene, and biphenyl radicals. The aromatic group may be a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthracenyl groups (n=3) and the like. The aromatic radical also may include non-aromatic components. For example, a benzyl group may be an aromatic radical, which includes a phenyl ring (the aromatic group) and a methylene group (the non-aromatic component). Similarly a tetrahydronaphthyl radical is an aromatic radical comprising an aromatic group ($C_6H_3$) fused to a non-aromatic component $-(CH_2)_4-$. An aromatic radical may include one or more functional groups, such as alkyl groups, alkenyl groups, alkynyl groups, haloalkyl groups, haloaromatic groups, conjugated dienyl groups, alcohol groups, ether groups, thio groups, aldehyde groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group, which is an alkyl group. Similarly, the 2-nitrophenyl group is a C6 aromatic radical comprising a nitro group, the nitro group being a functional group. Aromatic radicals include halogenated aromatic radicals such as trifluoromethylphenyl, hexafluoroisopropylidenebis(4-phen-1-yloxy) ($-OPhC(CF_3)_2PhO-$), chloromethylphenyl, 3-trifluorovinyl-2-thienyl, 3-trichloromethylphen-1-yl (3-$CCl_3Ph-$), 4-(3-bromoprop-1-yl)phen-1-yl ($BrCH_2CH_2CH_2Ph-$), and the like. Further examples of aromatic radicals include 4-allyloxyphen-1-oxy, 4-aminophen-1-yl ($H_2NPh-$), 3-aminocarbonylphen-1-yl ($NH_2COPh-$), 4-benzoylphen-1-yl, dicyanoisopropylidenebis(4-phen-1-yloxy) ($-OPhC(CN)_2PhO-$), 3-methylphen-1-yl, methylenebis(phen-4-yloxy) ($-OPhCH_2PhO-$), 2-ethylphen-1-yl, phenylethenyl, 3-formyl-2-thienyl, 2-hexyl-5-furanyl; hexamethylene-1,6-bis(phen-4-yloxy) ($-OPh(CH_2)_6PhO-$), 4-hydroxymethylphen-1-yl (4-$HOCH_2Ph-$), 4-mercaptomethylphen-1-yl (4-$HSCH_2Ph-$), 4-thiophenyl ($-S-Ph$), 4-methylthiophen-1-yl (4-$CH_3SPh-$), 3-methoxyphen-1-yl, 2-methoxycarbonylphen-1-yloxy (e.g., methyl salicyl), 2-nitromethylphen-1-yl (-$PhCH_2NO_2$), 3-trimethylsilylphen-1-yl, 4-t-butyldimethylsilylphenl-1-yl, 4-vinylphen-1-yl, vinylidenebis(phenyl), and the like. The term "a $C_3$-$C_{30}$ aromatic radical" includes aromatic radicals containing at least three but no more than 30 carbon atoms. The aromatic radical 1-imidazolyl ($C_3H_2N_2-$) represents a $C_3$ aromatic radical. The benzyl radical ($C_7H_7-$) represents a $C_7$ aromatic radical.

Many of the compounds described herein may contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, as well as, their racemic and optically pure forms. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

FTA paper is cellulose-based matrix impregnated with chemicals that lyse cells and preserve nucleic acid. The chemicals are activated when a biological fluid contacts the surface. Additional features of the chemical treatment are bacterial and viral inactivation. This protects the bio sample from microbial growth contamination and may also protect the user from potential biohazards present in the biosample. As such FTA paper is a preferred medium that protects and stabilizes DNA for collection, transport, storage, and archival from a variety of biological samples. The biological sample may then subsequently be analyzed. The analysis may include, but is not limited to genetic analysis or qualitative or quantitative determination of analytes present within the biological sample.

Biological samples, also refer to as genetic samples, may include both plant and animal tissue samples including, but not limited to, buccal (cheek) samples, cerebrospinal fluid, feces, plasma, blood, lymph, urine, seminal fluid, vaginal fluid, gland secretion, suspension of cells or viruses, viral plaques, or serum sample that contains nucleic acid. The sample may be in a purified state or from crude preparations such as a cell extract or culture, or directly obtained as a sample transfer such as a surface swabbing or spotting. The nucleic acids may include DNA and RNA, ribosomal RNA and messenger RNA, and nucleic acid primers and aptamers. Once a genetic sample is stored on the FTA paper, or a similar cellulose based material, it may be submitted for analysis using a number of protocols.

Analytes refers to one or more substances being measured in the biological sample. Analytes being measured in dried blood samples (DBS) may include quantitative or qualitative determination of circulating chemicals, drugs or metabolites. This may include, but is not limited to metabolites screening relating to the detection of a variety of metabolic diseases, drug metabolites relating to pharmacokinetic (DMPK) analysis for example with drug screening candidates, or chemical and drug exposure in toxicokinetics (TK) studies.

Analysis involving amplification or restriction enzyme digestion of the genetic material may be performed directly on the FTA paper, or a similar cellulose based material without the need for extraction procedures. In other instances extraction and purification of the genetic material from the paper may occur prior to analysis. This may be accomplished by washing a portion of the paper, such as a punch sample, with an extraction reagent.

However, regardless of the analysis, leachable components on the paper may be present which may interfere with the downstream analysis of the targeted analytes from the biological sample such as, but not limited to, compositional testing, drug discovery, and metabolites.

The structure of cellulose consists of parallel D-glucose chains. The structure is stabilized by hydrogen bonds giving it fibrous properties. The cellulose substrate may be in paper sheet, pulp form, tablet, or a cellulose powder prepared by either mechanical or chemical disintegration of alpha-cellulose, hard or soft wood pulp, purified wood pulp, cotton linter sheet, cotton pulp, or the like. Other sources of cellulose include low crystallinity celluloses and commercially available cellulose excipients, such as microfibrillated cellulose, powdered cellulose, regenerated cellulose, and microcrystalline cellulose. In certain embodiments the cellulose substrate may include nitrocellulose or carboxymethycellulose papers. It is preferred that the cellulose substrate be of a porous nature to facilitate immobilization of genetic material, storage, elution, and subsequent analysis.

In accordance with one embodiment, a method is described in which a cellulose substrate undergoes ring opening oxidation to form aldehyde groups at the $C_2$-$C_3$ position. In certain embodiments, in addition to ring opening oxidation at the $C_2$-$C_3$ position, oxidation of one or more hydroxyl groups present on the surface of the cellulose may also occur.

In certain embodiments ring opening oxidation of the cellulose substrate may occur through contact of the substrate with an oxidant such, but not limited to, gaseous chlorine, aqueous solutions of periodic acid and sodium hydroxide, persulfates, and permangenates. In other embodiments oxidation consists of consecutive oxidation with sodium periodate, and sodium chlorite. In other embodiments oxidation may involve enzymes. The oxidized cellulose may contain carboxylic acid groups, aldehyde groups, ketone groups, or a combination thereof in addition to hydroxyl groups of the untreated substrate. The amount of oxidation depends on the nature of the oxidant and the reaction conditions.

The cellulose substrate may be oxidized just prior to subsequent reaction with the aminooxy reagents. In other embodiments, a cellulose substrate having a certain degree of oxidation may be used available and stored from a prior oxidation treatment or from a commercial source.

In certain embodiments, the oxidized cellulose substrate is subsequently treated with an aminooxy reagent having a terminal sulfate group (—$OSO_3H$), sulfonate group (—$SO_3H$) or a carboxylic acid group (—COOH). Aminooxylation of one or more of the aldehyde groups occur to form pendent alpha-oximocarboxamide groups on the cellulose surface. Aminooxylation occurs at the $C_2$ position, $C_3$ position or both. In certain embodiments, aminooxylation may also occur at surface aldehyde groups, which resulted from oxidation of pendent hydroxyl groups on the cellulose surface.

Scheme 1 illustrates aminooxylation at both the $C_2$ and $C_3$ position.

Scheme 1: Aminooxylation at the ring opened C2 and C3 and positions.

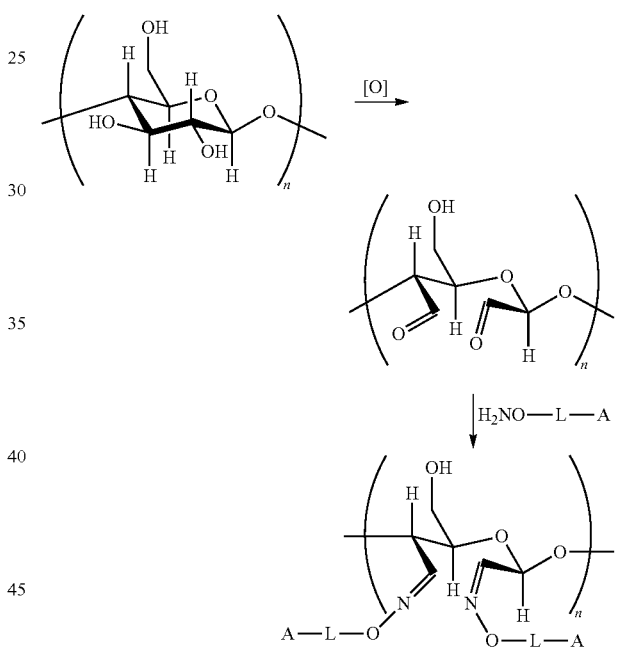

This results in a modified cellulose substrate comprising structural units of Formula I $$-\!\!\operatorname*{\left(CH-CH_2(CH_2OH)-O-CH-O\right)\!\!-}_{\underset{CH=X}{|}\qquad\qquad\qquad\underset{CH=Y}{|}}$$

wherein X and Y are independently N—O-L-A or O, with the proviso that when Y is O, then X is N—O-L-A, and when X is O, then Y is N—O-L-A; L is a direct bond, an aliphatic radical, an aromatic radical, a cycloaliphatic radical, or a combination thereof; and A=COOH, $SO_3H$, or a combination thereof.

In certain embodiments, the aminooxy reagent may comprise
a substituted aminooxy of Formula II wherein;

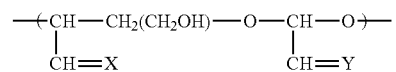

(II)

L is a direct bond, an aliphatic radical, an aromatic radical, a cycloaliphatic radical, or a mixture thereof; and A=COOH, SO$_3$H, or a mixture thereof.

In certain embodiment, L may be a disubstituted $(CH_2)_n$ aliphatic radical wherein, n is an integer between 1 and 20. The aliphatic radical may be a linear or branched array of atoms.

In certain embodiments L may be heteroatom substituted. In certain embodiments L may be equal to —$(CH_2)_n$—Z—$(CH_2)_m$— wherein n is an integer between 0 and 20, m is an integer between 0 and 20, and X is a heteroatom containing moiety. In certain embodiments, Z may equal, but not limited to; O, NH, C(O)NH, NHC(O), N(CO)N, O(CO)O, N(CS)N, O(CS)O, or a combination thereof. In each embodiment L links a sulfonate group (—SO$_3$H), a carboxylic acid group (—COOH), or, when L is a direct link, a terminal sulfate group to the oximocarboxamide moiety. For example, Z is O, n is 0, m is 1 and A is COOH.

The aminooxy reagent may be used as an aqueous solution of its salts. Salts include, but are not limited to, sulfates, nitrates, hydrohalides, and phosphates. In certain embodiments the aqueous solutions range from 0.05 to 0.5 mol % aminooxy. In certain embodiments, alcohol co-solvents may be used. In another embodiment, the aqueous solution may also contain a buffer solution. In other embodiments the aqueous solution may also contain a stabilizer.

A method of applying the aminooxy reagent may include contacting the aminooxy reagent with the oxidized cellulose substrate such that a chemical reaction involving binding of the aminooxy reagent to the oxidized cellulose. In one embodiment, an aminooxy reagent may be contacted with the oxidized cellulose substrate by dipping the oxidized cellulose substrate in a solution of the aminooxy reagent. In another embodiment the aminooxy reagent may be applied to the oxidized cellulose by spraying, wetting, or printing onto the surface. Solutions of aminooxy reagent, if employed may include solvents having sufficiently volatility to allow for evaporation of the solvent.

In one embodiment, the oxidized cellulose substrate may be in a powder form. As such slurry containing both the aminooxy reagent and the oxidized cellulose may be used to allow contact and binding. The slurry may be decanted, pressed, and dried to yield an oxidized powder.

In one embodiment, the binding may be initiated at room temperature. In another embodiment, binding may be initiated by applying heat. In certain embodiment the temperature ranges from about 40° C. to about 90° C.

The binding of the reagent is conducted for a time sufficient to react the aminooxy compound of Formula I with the aldehyde groups on the oxidized cellulose substrate. In one embodiment, the reaction is conducted for a time period ranging from about 1 min to about 30. In another embodiment, the time period ranges from about 1 min to about 10 min. The reaction may be carried out under ordinary pressure or pressurized conditions.

An article may be fabricated employing the compositions and methods described hereinabove. In one embodiment, an article is provided. An article includes reaction product of oxidized cellulose having binding sites and an aminooxy reagent. In one embodiment, an article fabricated employing the compositions and methods disclosed herein may have a thickness that is greater than about 0.1 millimeters, greater than about 0.5 millimeters, greater than about 1 millimeters, or greater than about 0.5 centimeter. In one embodiment, the article may be in powder form and contained in an appropriate sized sample vial. In still another embodiment, the article may be in the shape of a tablet. In still other embodiments the article may be in a gel or solution.

In other embodiments, additional treatment of the oxidized cellulose substrate may occur, including but not limited to applying chemical coating solutions such as protein denaturing agents and a free radical trap. The denaturing agents can be a surfactant or anionic detergents that will denature proteins and pathogenic organisms in the genetic sample. The denaturing agents also act to lyse the genetic material and allow the genetic material to be immobilized and preserved. In certain embodiments the denaturing agent acts to lyse the cells containing the genetic material to release analytes of interest. The chemical solution may include a weak base, chelating agents, and an anionic surfactant or detergent. Uric acids and urate salts may also be used. A weak base may be a Tris, trishydroxymethyl methane, either as a free base or as the carbonate, and the chelating agent maybe EDTA. The anionic detergent may be sodium dodecyl sufate or sodium lauryl sulfate. Other coatings having similar functions may also be used. For example in certain embodiment a coating may be used that is capable of lysing the cells but does not denature proteins In other embodiments, the coating may act to deactivate enzymes without denaturing for instance, by chelating metals that act of cofactors for enzymes function.

In certain embodiments, the coating solutions may be applied to the substrate in such a matter that the coatings are disposed, sorbed, or otherwise associated with the oxidized cellulose. In certain embodiments the coatings may adhere to the substrate through chemical bonding while in other embodiments, adherence may be physical such as through impregnation.

In certain embodiments, the aminooxy reagent is applied prior to other chemical treatments. In other embodiments, the aminooxy reagent is applied subsequent to the other chemical treatments. In still other embodiments the aminooxy reagent is applied as an intermediate step.

The modified oxidized cellulose substrate may be used as a method for storage of a genetic material that is contacted with the substrate. In certain embodiments, the method involves contacting the genetic material to the substrate. The genetic material may include both plant and animal tissue samples including, but not limited to, buccal (cheek) samples, cerebrospinal fluid, feces, plasma, blood, lymph, urine, suspension of cells or viruses, viral plaques, or serum sample that contains nucleic acid.

The modified cellulose substrate may also be used as a method for storage of, but not limited to, small drugs and metabolites that could be incorporated in applications, such as DMPK. In a preclinical setting, the ability to store analyte samples contained in biological media for example using a dried blood spot (DBS) approach, may simplify the experimental workflow. This may be accomplished by decreasing the volume of biological samples needed and consequently minimizes the number and size of animal subjects used, while the analytes are being preserved for later analytes. Simplification in experimental workflow may also reduce the possibility of human error.

The genetic sample may be in a purified state or from crude preparations such as a cell extract or culture, or directly obtained as a sample transfer such as a surface swabbing or spotting. The nucleic acids may include, but is not limited to, DNA and RNA, ribosomal RNA and messenger RNA, or nucleic acid primers and aptamers.

In certain embodiments, the modified oxidized cellulose substrate is shaped into an article, which will facilitate the storage of the genetic material. The article may be in the form of a paper, tablet, or powder. In certain embodiments, a paper form may be used which may be such as a card stock wherein samples contacted with the form may be subsequently removed for example by punching through the card stock. In other embodiments, the article may be in the form of a powder contained within a sample tube or vial. The sample tube or vial may be sized to match the size of the genetic sample or analyte and allow subsequent reagents or extraction techniques to be added directly to the article to allow for genetic incubation, amplification, or other testing. In another embodiment, the article may be in form of a tablet wherein the tablet, based on different compaction pressures, may have different physical properties, such as pore size distribution and surface area.

As an article, desirable properties of the cellulose substrate useful for collecting, storing, and preserving a biological sample may include low leachable components, antibacterial properties, antiviral properties, and efficient wicking properties.

In certain embodiments, the modified oxidized cellulose substrate may have lower levels of leachable as compared to other similarly formed cellulose articles. Leachables are defined as residual chemicals that may be present on or within the cellulose substrate that may be leached or extracted from the substrate during subsequent processing of the genetic sample, such that the residual may be present in the isolated genetic sample and interfere with downstream analysis. The level of leachables may be measured as extractables from the cellulose substrate using a solvent washing wherein the solvent dissolves or extracts materials from the cellulose substrate. In certain embodiments, the no leachable substrate may be defined as having less than 200 ppm, preferably less than 100 ppm, and more preferable less than 25 ppm of extractables in the washed solution. As such a nonleachable composition or article formed from a nonleachable composition means that the composition is relatively free of residuals such that the residuals do not have a potential for contaminating the genetic sample. In the case of DMPK application, leachables and extractables that can interfere with the analysis of metabolites or analytes of interest are not desired.

The various chemistries and formulations used to modify the cellulose substrate are shown in TABLE 1. Whatman 31ETF is a smooth cellulose paper that has not been treated, [O]ETF is 31ETF subjected to C2 and C3 and ring opening surface oxidation by treatment with $NaIO_4$. FTA® is a commercially available paper used for genetic sampling and treated with TRIS, EDTA, uric acid, and sodium dodecyl sulfate.

TABLE 1

| Chemical Modification | | |
|---|---|---|
| Approach | Designation | Structure |
| AminoOxy/Amine | S | $H_2N-O-S(=O)_2-OH$ |
| | C | $H_2N-O-CH_2-C(=O)-OH$ |

TABLE 1-continued

| Chemical Modification | | |
|---|---|---|
| Approach | Designation | Structure |
| | T | $H_2N-O-CH_2-C(=O)-NH-CH_2CH_2-S(=O)_2-OH$ |
| | D | $H_2N-(CH_2)_{10}-$ |
| Polymeric Radical | 1 | (copolymer structure with w, x, y, z; carbamate, sulfonate $O^-Na^+$, OH, and $HN(CH_2)_7CH_3$ groups; methacrylate pendant) |
| | 2 | (copolymer structure with w, x, y, z; carbamate with methacrylate, OH, sulfonate $O^-Na^+$) |
| Quat amines Radical | 3 | (methacrylate ester with $-OCH_2CH_2-N^+(CH_3)_2-CH_2Ph$) |

1b; w = 0.02, x = 0.45, y = 0.33, z = 0.2
1d; w = 0.02, x = 0.38, y = 0.33, z = 0.27
2; w = 0.02, x = 0.28, y = 0.54, z = 0.16
3a = 26 wt % add on, e-beam initiation
3b = 9% wt % add on, ceric ammonium nitrate initiation The degree of leachability for the different chemistries and formulations tested on cellulose paper or oxidized cellulose, was determined by subjecting the various papers to extraction with 70% aqueous tetrahydrofuran. The extracts where identified and quantified using LC-MS methodology. Extractables analyses showed that in contrast to other chemistries, the cellulose that was derivatized by means of aminooxy chemistry shows relatively no extractables from the cellulose paper. This result is comparable to the negative control (31ETF) shown in FIG. 1 as a liquid chromatographic trace. As shown, 31ETF shows no extractables, in contrast to the positive control (FTA paper) that contains a mixture of molecules impregnated on the surface and shows extractables that may interfere with metabolite analysis. The formulation involving the use of a combination of aminooxy "S" and amine molecule "D" (S-D) showed that the aminooxy molecule, that forms an oxime linkage with the oxidized cellulose paper, does not have extractables (non leaching), whereas the amine molecule that forms a Schiff base, from a quaternary amine salt, with the oxidized cellulose paper does. Further, the samples having only aminooxy molecules present in the formulation (S, C, T) do not show extractables.

These results may be explained in part by the non-reversible character of an oxime linkage as compared to the reversible character of an Schiff base. In the formulations involving quaternary amines, extractables were corresponding both to the monomeric unit used and hydrolysis products. Hence, these results suggest that the oxime modification chemistry may be a preferred method to render non-leachable properties.

In certain embodiments, the modified oxidized cellulose may have antibacterial and antiviral properties, comparable or better than commercial FTA paper. These properties minimize the need for highly regulated safety classifications and guidelines in procedures involving the handling of biological samples. This may translates into lower cost, simplified processes that may involve the use, storage and transportation of biological samples. In addition, antibacterial properties of the paper may minimize the potential growth of bacteria that may damage the biological samples upon storage.

The antibacterial properties of various modified oxidized cellulose formulations were evaluated against three different strains that represent both gram positive and gram-negative strains, as well multidrug resistant strains. Table 2 summarizes the results from a replica plating assay and show that the oxidized paper modified with aminooxy/amine moieties show the highest antibacterial activity, as compared against non-modified cellulose substrates and representative examples of formulations prepared using a radical chemical approach to immobilize polymeric or quaternary amine-based formulations. Hence, the antibacterial character is a result of the modification step, not the preceding oxidation step. The polymeric molecules showed no antibacterial activity, while the family of quaternary amines showed strain-dependant results, but still rather mild. As depicted in Table 2 no antibacterial activity is indicated as (−), minimal inhibition of bacterial grown (+), partial inhibition of bacterial growth (++), and complete inhibition of bacterial growth as (+++).

TABLE 2

Antibacterial property results

| Sample Family | Gram+ MRSA | Gram− P. | Gram− E. Coli |
|---|---|---|---|
| Controls | | | |
| 31ETF | − | − | − |
| FTA | +++ | +++ | +++ |
| [O] 31ETF | − | − | − |
| Aminooxy/Amine | | | |
| D-S | +++ | +++ | +++ |
| S | +++ | +++ | +++ |
| C | +++ | +++ | +++ |
| T | ++ | +++ | ++ |
| Polymeric | | | |
| 1b | − | − | − |
| 1d | − | − | − |
| 2 | − | − | − |
| Quaternary amine | | | |
| 3a | + | − | +++ |
| 3b | + | − | +++ |

In applications involving the collection of biological samples, the ability of the paper to wick, or to flow the biological sample through the paper in a wetting type of action, rapidly and homogeneously is important in order to ensure a reliable and reproducible sample reading. In certain embodiments, the modified oxidized cellulose has the desired wicking properties whereby the wicking properties are comparable to commercial FTA paper.

FIG. 2. is a graphical representation of how quickly the different samples of modified paper can absorb 10 uL of whole blood. The control cellulose papers (31ETF, FTA and [O]31ETF) were shown to absorb 10 uL of whole blood in the range of 3-4 seconds. 31ETF and [O]31ETF papers were modified using different families of molecules and formulations as shown previously in TABLE 1. Formulations involving the use of polymeric (SDS-like) molecules rendered a rather hydrophobic surface despite the hydrophilic and water soluble character of the molecules prior to their immobilization onto the cellulose paper using an approach involving radical chemistry. Nevertheless, the oxidized cellulose paper that was reacted with the aminooxy and amine molecules, as well as the quaternary amine formulations involving radical chemistry on the non-oxidized cellulose paper (31ETF), showed results comparable to the controls.

The invention includes embodiments that relate generally to methods applicable in analytical, diagnostic, or prognostic applications such as, but not limited to, forensics, transgenic identification, transfusion medicine/HLA typing, plasmid screening, food and agriculture testing, drug discovery, genomics, STR analysis, animal identification, whole genome amplification, and molecular biology. In some embodiments, the methods disclosed herein may be particularly applicable in DMPK analysis.

EXPERIMENTAL

General Procedure for Oxidizing Cellulose

Whatman grade 31ETF cellulose supplied by GE Healthcare was submerged in an aqueous solution of $NaIO_4$ and allowed to react at a given temperature for a predetermined time. Temperature varied but typically varied from 1 to 5 minutes at 50 to 90° C. The fully wetted out membranes were then washed in deionized water until the conductivity of the aqueous washes were less than 3 µS. Samples were then dried at room temperature overnight.

General Procedure for Reacting Aminooxy Compounds (AO) with Oxidized Cellulose

Oxidized 31ETF cellulose samples were pre-weighed and then submerged in an aqueous solution of the aminooxy compound at room temperature. Following complete wet-out, the samples were removed from the solution with tweezers, and excess solution was allowed to drain from the saturated membrane. The samples were then partially dried with a heat gun, and placed in crystallization dishes to be dried at a predetermined temperature and time. Typically samples were dried at room temperature or in a warm circulating air oven between 50° and 70° C. for a period of 12 to 24 hours. The samples were weighed following drying, washed with deionized water, and solution conductivity was recorded. The samples were redried at the same predetermined oven temperature for approximately 1 hour, and rewashed with deionized water. This process was repeated until the ion conductivity was less than 3 µS. The samples were redried at the same predetermined temperature, and a final weight was recorded. Weight percent add-ons were determined by the following equation:

Weight percent add-on=(Final weight−initial weight)/initial weight*100%

Samples were also characterized by elemental analysis. Either elemental sulfur or nitrogen content was determined to deduce the extent of aminooxy (AO) functionalization.

Procedure for Sample 4a in AO-CO2H DOE

A 14 cm×14 cm 31ETF cellulose sheet was submerged in a 1.0 M aqueous solution of $NaIO_4$ at 80° C. and allowed to react for 5 minutes. The fully wetted out membranes were then washed in deionized water until the conductivity of the aqueous washes were less than 3 µS. The oxidized 31ETF cellulose was then dried at room temperature overnight. The 14 cm×14 cm sheet was then cut up into multiple 6 cm×4 cm sheets for the subsequent treatment with the aminooxy reagents. A 6 cm×4 cm sheet was submerged in an aqueous 0.2 M aminooxy reagents solution at room temperature. Following complete wet-out, the samples were removed from the solution with tweezers, and excess solution was allowed to drain from the saturated membrane. The samples were then partially dried with a heat gun, and placed in crystallization dishes to be dried at 60° C. overnight. The sample turned a brown color upon heating overnight. The dried sample was weighed, washed with deionized water, and solution conductivity was recorded. The sample was redried at 60° C. for one hour, and rewashed with deionized water. This process was repeated until the ion conductivity was less than 3 µS. The sample was submitted for nitrogen elemental analysis to determine the extent of covalently attached aminooxy moieties. Elemental Nitrogen Analysis, results are expressed as N % in the sample as submitted ± the 95% confidence intervals (CI).

Sample Preparation

Samples were submitted as approx. ¾" squares, two squares per sample type. A razor blade, pre-cleaned with IPA, cut the samples into tiny squares. Using a microbalance, each sample replicate was weighed into a tared 5×9 mm tin capsule, which was then squeezed into a small, capsule-enclosed ball, and weighed again. The weight of each sample type varied dependent upon approx. nitrogen concentration. Two tin capsule blanks were carried through the analysis.

Standards

A CHN calibration was performed on an EA1108 Elemental Analyzer (Thermo Scientific, Waltham, Mass.) using THAB (1.407% N) as standard material. An 8pt calibration (0.068 mg, 0.187 mg, 0.416 mg, 0.826 mg, 1.552 mg, 2.404 mg, 3.450 mg, 6.323 mg) produced a nitrogen curve with a R2=99.98%. A second standard material (atropine, 4.84% N) was analyzed, in addition to the THAB, as unknowns to verify the accuracy of the calibration curve. THAB nitrogen recovery: 97%-109%. Atropine nitrogen recovery: 96%-106%.

Experimental Technique

The samples were analyzed 4×'s on the Carlo Erba EA1108 Analyzer for N. The technique is based on a quantitative flash combustion of the sample at 100° C. in an oxygen-enriched atmosphere to form $CO_2$, $H_2O$, and NOx, from nitrogen, carbon, hydrogen, and sulfur respectively. The combustion gases are passed through heated elemental copper to reduce all forms of NOx to $N_2$. They are then carried through a chromatographic column by the carrier gas where they are separated and detected by a thermal conductivity detector for quantification. The analyte concentration is calculated by comparison with a series of known standards. The calibration is prepared as total mg analyte, which is converted to % based on the weight of sample analyzed. (Instrumental Parameters: Helium flow set to 150 mL/min, Oxygen flow set to 60 mL/min, 540 seconds per sample. Elemental Sulfur Analysis results were determined measuring wt % metals in cellulose paper at a 95% confidence intervals (CI) to verify surface modification. Sample Preparation Microwave vessels were pre-cleaned once with 10 mL $HNO_3$ acid using one microwave cycle. One replicates of 0.06-0.09 g samples (the entire sample submitted was used for one replicate) were weighed by difference and placed into Teflon XP1500 microwave liners. 10 ml $HNO_3$ acid was added, washing down the liner walls. The liners were capped, placed into microwave, and run with "paper" program (10-minute ramp to 100° C.; hold at 100° C. for 10 minutes; pressure control to 100 psi, 10 minute ramp to 150° C.; hold at 150° C. for 10 minutes; pressure control to 200 psi, minute ramp to 180° C.; hold at 180° C. for 10 minutes; pressure control to 300 psi, minute ramp to 200° C.; hold at 200° C. for 10 minutes; pressure control to 400 psi, 10 minute ramp to 220° C.; hold at 220° C. for 10 minutes; pressure control to 600 psi,). After heating cycle samples were allowed to cool completely to room temperature before opening. Vessel contents transferred to orange cap tube, 5 mL of 10 ppm Sc was added, and the solution diluted to 50 mL with deionized water (DIW). A blank and a sample spike were carried throughout the procedure. Acid Spike Recovery: S: 110%. Spex QC Recovery: S: 102%. Standards: S: 0.05 ppm-10 ppm in 50 ml orange-cap plastic tubes with 20% $HNO_3$ with 1 ppm Sc. QC1: 1 ppm Spex4. Rinse: 20% $HNO_3$.

Technique: Spectro Arcos ICP-AES

High temperature plasma is produced by inductively coupling radio frequency power into a stream of argon gas. The samples are introduced as a solution aerosol into the plasma by a nebulizer where the respective elements emit their characteristic radiation. In the optics, the Arcos utilizes 32 linear CCD detectors in an optimized Paschen-Runge mount ORCA (Optimized Rowland Circle Alignment) (SPECTRO Analytical Instruments GmbH, Germany) for the simultaneous recording of the wavelengths between 130 and 770 nm. The magnitude of the signal is directly proportional to the concentration of an element in a sample. Comparing sample signal intensities to those generated by calibration standards produces quantitative results.

Replica Plating Assay (Antibacterial Assay) Experimental

Anti-bacterial properties were evaluated using the Gram-negative bacterium *Pseudomonas aeruginosa* (infecting isolate 09-010, Brooke Army Medical Center Molecular Biology Lab and US Army Institute of Surgical Research), the Gram-positive bacterium MRSA USA300 (methicillin-resistant *Staphylococcus aureus* infecting isolate NRS384, Network on Antimicrobial Resistance in *Staphylococcus aureus*), and lab-strain *Escherichia coli* (HB101). Inoculates were cultured in Luria Broth for >6 hours until mid-late log phase (0.6-1.2 OD600), at which time culture density was estimated using a 0.5 McFarland standard. Approximately 1-2×107 cells (14-20 µL of culture) were applied to a 7 mm punch of grafted 31-ETF as well as positive (FTA) and negative (31-ETF) control paper, and samples were air-dried for 30 minutes (clinical isolates) or 60-90 minutes (lab-strain *E. coli*). Using sterile forceps, samples were replica-plated to fresh trypticase soy agar (TSA) by inverting each punch onto the agar surface and gently pressing. Punch samples were removed prior to incubating the plate overnight at 37° C., and bacterial growth was assessed after 12-24 hours.

Analysis of Extractable Reagents from 31-ETF Oxidized Substrates by HPLC-Electro Spray ToFMS:

Paper circular punches, 7 mm in diameter, were extracted with 500 uL of 70 THF in water, using vortex for 1 min. The chromatographic analysis of extractables was achieved using an Agilent 1200 Series HPLC system equipped with a 1200 Series Photo-Diode Array detector in-line to an AB Sciex Q Star Elite® Quadropole Time of Flight Mass Spectrometer equipped with an Electro Spray ionization accessory. The separation was carried out using a Cadenza CL C18 1×50 mm reverse phase column consisting of 3 um particle media. Electro spray ionization mass spectra were acquired in positive ionization mode. The quantitative analysis was obtained from the integrated peak area of extracted mass chromatograms of known masses of the respective reference materials. The method parameters were as follows: Mobile Phase: Solvent A, 2 mM Ammonium Formate (pH=4); Solvent B, 100% acetonitrile containing 0.1% formic acid; Flow Rate: 0.2 ml min−1; Photodiode Array Detector Acquisition: 200-800 nm; Column: Cadenza CL C18 3 um (1×50 mm); Injection Volume: 50 ul; ESI Conditions: Neb Gas: 40, Drying Gas: 40, Applied Needle Voltage: 3000V, Temperature: 400° C.

The invention may be embodied in other specific forms without departing from the spirit or essential characteristics thereof. The foregoing embodiments are therefore to be considered in all respects as illustrative rather than limiting on the invention described herein. The scope of the invention is thus indicated by the appended claims rather than by the foregoing description, and all changes that come within the meaning and range of equivalency of the claims are therefore intended to be embraced therein.

The invention claimed is:

1. An article for storing genetic material or analytes from a biological sample comprising:
a cellulose substrate comprising structural units of Formula I

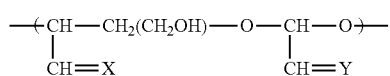
(I)

wherein;
X and Y are independently N—O-L-A or O, with the proviso that when Y is O, then X is N—O-L-A, and when X is O, then Y is N—O-L-A; and
L is a direct bond, an aliphatic radical, an aromatic radical, a cycloaliphatic radical, or a combination thereof; and
A=COOH, SO3H, or a combination thereof.

2. The article of claim 1 wherein L is equal to $(CH_2)_n$ and n is an integer between 1 and 20.

3. The article of claim 1 wherein L is a direct bond and A is $SO_3H$.

4. The article of claim 1 wherein L is heteroatom substituted.

5. The article of claim 4 wherein:
L is —$(CH_2)_n$—Z—$(CH_2)_m$—;
n is an integer between 0 and 20;
m is an integer between 0 and 20; and
Z is equal to O, NH, C(O)NH, NHC(O), N(CO)N, O(CO)O, N(CS)N, O(CS)O or a combination thereof.

6. The article of claim 5 wherein Z is O, n is 0, m is 1 and A is COOH.

7. The article of claim 1 further comprising a chemical coating adhered to the cellulose substrate, said coating capable of denaturing proteins, deactivating enzymes, or a combination thereof.

8. The article of claim 7 wherein the chemical coating comprises a surfactant, anionic detergent, a weak base, a chelating agent, a free radical trap, uric acid, urate salts, and combinations thereof.

9. The article of claim 1 wherein the article is a paper, tablet, or powder.

* * * * *